United States Patent
Bugnon et al.

(10) Patent No.: US 9,938,419 B2
(45) Date of Patent: *Apr. 10, 2018

(54) PIGMENT COMPOSITION

(71) Applicant: BASF SE, Ludwigshafen (DE)

(72) Inventors: Philippe Bugnon, Le Mouret (CH); Karin Karrer, Pfeffingen (CH)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/513,209

(22) PCT Filed: Aug. 14, 2015

(86) PCT No.: PCT/EP2015/068751
§ 371 (c)(1),
(2) Date: Mar. 22, 2017

(87) PCT Pub. No.: WO2016/045874
PCT Pub. Date: Mar. 31, 2016

(65) Prior Publication Data
US 2017/0253753 A1    Sep. 7, 2017

(30) Foreign Application Priority Data

Sep. 23, 2014  (EP) .................... 14185875

(51) Int. Cl.
C09D 11/03      (2014.01)
C09B 67/04      (2006.01)
(Continued)

(52) U.S. Cl.
CPC .......... C09D 11/037 (2013.01); C07D 401/04 (2013.01); C07D 471/04 (2013.01);
(Continued)

(58) Field of Classification Search
CPC ... C09B 67/00; C09B 67/0001; C09B 67/002; C09B 67/0002; C09B 67/0022;
(Continued)

(56) References Cited

U.S. PATENT DOCUMENTS 4,622,391 A    11/1986  Lorenz et al.
4,628,082 A    12/1986  Lorenz et al.
(Continued)

FOREIGN PATENT DOCUMENTS

| DE | 10 2006 032 591 A1 | 1/2008 |
| EP | 0 073 463 A1 | 3/1983 |
| EP | 0 485 337 A1 | 5/1992 |
| EP | 0 902 061 A2 | 3/1999 |
| EP | 0 994 162 A1 | 4/2000 |
| EP | 0 994 164 A1 | 4/2000 |
| EP | 1 086 992 A1 | 3/2001 |
| EP | 1 474 484 | 11/2004 |
| EP | 1 612 246 A1 | 1/2006 |
| EP | 2 682 434 A1 | 1/2014 |
| WO | 02/10288 A1 | 2/2002 |
| WO | 03/064540 A1 | 8/2003 |
| WO | 2009/144115 A1 | 12/2009 |

OTHER PUBLICATIONS

International Search Report dated Oct. 12, 2015 in PCT/EP2015/068751 filed Aug. 14, 2015.
Extended European Search Report dated Mar. 12, 2015 in Patent Application No. 14185875.3.
International Preliminary Report on Patentability and Written Opinion dated Apr. 6, 2017 in PCT/EP2015/068751.
International Search Report and Written Opinion dated Oct. 12, 2015 in PCT/EP2015/068751.
John C. MacDonald, et al., "Solid-State Structures of Hydrogen-Bonded Tapes Based on Cyclic Secondary Diamides", Chemical Reviews, vol. 94, Issue 8, 1994, pp. 2383-2420.
Jonathan A. Zerkowski, et al., "Design of Organic Structures in the Solid State: Hydrogen-Bonded Molecular "Tapes"", Journal of the American Chemical Society, vol. 112, Issue 24, 1990, pp. 9025-9026.

*Primary Examiner* — Anthony J Green
(74) *Attorney, Agent, or Firm* — Oblon, McClelland, Maier & Neustadt, L.L.P.

(57) ABSTRACT

A pigment composition is provided comprising (a) an organic pigment and (b) an adduct containing a compound of formula (I) or a tautomeric form thereof, wherein X is O or S; Y is O, S or $NR^1$; the group -A-B— is selected from the group consisting of $-CR^2=CR^3-$, $-CR^4R^5-CR^6R^7-$, $-CY-CR^8R^9-$, $-CX-NR^{10}-$, $-CR^{11}=N-$, $-CR^{12}R^{13}-NR^{14}-$ and $R^1$ is hydrogen, $C_1$-$C_8$alkyl, $C_3$-$C_7$cycloalkyl, $C_6$-$C_{10}$aryl or $C_7$-$C_{10}$aralkyl; $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, halogen, $C_1$-$C_8$alkyl, $C_2$-$C_8$alkenyl or $C_6$-$C_{10}$aryl, or $R^2$ and $R^3$ form a benzoannellated ring; and/or a melamine- or pyrimidine-based compound, which is optionally substituted. The pigment composition may be used as colorant in various applications, especially in coloring high molecular weight organic material, for example, coating compositions, paints, printing inks, liquid inks, plastics, films or fibers.

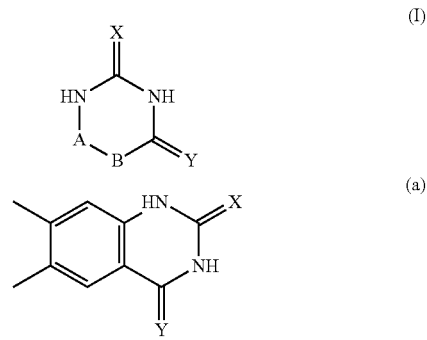

20 Claims, No Drawings

(51) Int. Cl.
    *C09D 11/037*     (2014.01)
    *C09B 67/18*     (2006.01)
    *C09B 67/46*     (2006.01)
    *C09D 11/322*     (2014.01)
    *C07D 471/04*     (2006.01)
    *C07D 401/04*     (2006.01)

(52) U.S. Cl.
    CPC ........ *C09B 67/0002* (2013.01); *C09B 67/002* (2013.01); *C09B 67/0089* (2013.01); *C09D 11/322* (2013.01)

(58) Field of Classification Search
    CPC ............ C09B 67/0023; C09B 67/0032; C09B 67/0034; C09B 67/006; C09B 67/0089; C09D 11/037; C09D 11/322; C07D 471/04; C07D 401/04
    See application file for complete search history.

(56) References Cited

U.S. PATENT DOCUMENTS

| | | |
|---|---|---|
| 6,261,358 B1 | 7/2001 | Sommer et al. |
| 6,281,338 B1 | 8/2001 | Sommer et al. |
| 2003/0172847 A1 | 9/2003 | He et al. |
| 2004/0215015 A1 | 10/2004 | Nazarov et al. |
| 2006/0000391 A1 | 1/2006 | Hamada |
| 2007/0020408 A1 | 1/2007 | Feldhues et al. |
| 2007/0020409 A1 | 1/2007 | Feldhues et al. |
| 2007/0151478 A1 | 7/2007 | Erk et al. |
| 2008/0057417 A1 | 3/2008 | Feldhues et al. |
| 2014/0016072 A1 | 1/2014 | Borst et al. |

PIGMENT COMPOSITION

The present invention relates to a pigment composition comprising an organic pigment modified by a hydrogen-bonded, stabilized adduct, to a process for preparing the same and the use thereof as a colorant in various applications, especially in coloring high molecular weight organic material, for example, coating compositions, paints, printing inks, liquid inks, plastics, films or fibers.

Usually, crude pigments are subjected to one or more conditioning steps which modify particle size, crystal structure and/or surface properties in order that the pigment can be appropriately utilized. A variety of techniques have been developed, for example, grinding procedures with suitable grinding agents in the presence or absence of organic solvents, inorganic or organic encapsulation, adsorption of a polymer, rosination, adsorption of a pigment derivative, grafting of a specific reactant onto the pigment or the like.

Hence, there is a continuing need for suitable pigmentary forms based on organic pigments having improved coloristic properties, especially high chroma and color strength, wherein the amount of the organic pigment may be reduced.

Therefore, it is an object of the present invention to provide an organic pigment composition exhibiting the desired coloristic properties, especially improved chroma and/or color strength.

Inclusion compounds, intercalation compounds and solid solutions of metal complexes based on azo-barbituric acid or derivatives thereof, such as C.I. Pigment Yellow 150, with various guest compounds have already been described. For example, U.S. Pat. No. 4,622,391 or U.S. Pat. No. 4,628,082 describes various organic compounds to be embedded in metal complexes based on Pigment Yellow 150, e.g., urea derivatives, surfactants, natural resins or resin acids, water-soluble polymers, or dyestuffs.

Various processes for preparing melamine-hosting pigments based on Pigment Yellow 150 are disclosed, for example, in EP-A-994162 and EP-A-994164. The pigments are described as soft in texture and thus good to disperse in application media. US-A-2008/0057417 discloses a process in order to improve reproducibility, wherein a mixture of mono- and dipotassium complex of azo-barbituric acid with a nickel compound and melamine is reacted. Likewise, US-A-2007/0020408 discloses a process for preparation of such host-guest compounds in the presence of seed crystals, and US-A-2007/0020409 discloses a process for preparation using a heat treatment step in at least two pH stages. For example, Levascreen® Yellow G is a commercially available Pigment Yellow 150 hosting melamine.

EP-A-1612246 discloses a pigment inclusion complex comprising an azo-barbituric acid metal complex, melamine and tert-amine substituted melamine derivative. The resulting paints and inks are described as having good flowability without causing agglomeration.

EP-A-2682434 discloses a melamine adduct of a zinc/nickel azo-barbituric acid hybrid compound for shading green pigment in color filter applications.

It is further known that melamine and cyanuric acid form a solid structure based on strong hydrogen bonds, also described as 1:1 co-crystals by G. M. Whitesides et al. in J. Am. Chem. Soc. 112 (1990), 9025-9026. A variety of similar solid-state structures of hydrogen-bonded tapes based on cyclic secondary diamides have been described by J. C. MacDonald and G. M. Whitesides in Chem. Rev. 94 (1994) 2383-2420.

It has now been found that a pigment composition based on an organic pigment having the desired properties may be obtained by modifying said pigment with a hydrogen-bonded, stabilized adduct.

Accordingly, in a first aspect the invention relates to a pigment composition comprising
(a) an organic pigment and
(b) an adduct selected from
(b1) an adduct containing a compound of formula

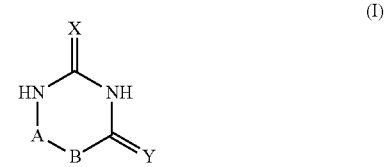

or a tautomeric form thereof, wherein
X is O, S or NR$^1$, preferably X is O or S;
Y is O, S or NR$^1$;
-A-B— is selected from the group consisting of —CR$^2$=CR$^3$—, —CR$^4$R$^5$—CR$^6$R$^7$—, —CY—CR$^8$R$^9$—, —CX—NR$^{10}$—, —CR$^{11}$=N—, —CR$^{12}$R$^{13}$—NR$^{14}$— and

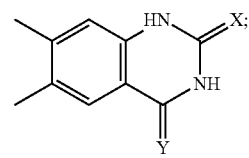

R$^1$ is hydrogen, C$_1$-C$_8$alkyl, C$_3$-C$_7$cycloalkyl, C$_6$-C$_{10}$aryl or C$_7$-C$_{10}$aralkyl;
R$^2$, R$^3$, R$^4$, R$^5$, R$^6$, R$^7$, R$^8$, R$^9$, R$^{10}$, R$^{11}$, R$^{12}$, R$^{13}$ and R$^{14}$ are independently of each other hydrogen, halogen, C$_1$-C$_8$alkyl, C$_2$-C$_8$alkenyl or C$_6$-C$_{10}$aryl, or
R$^2$ and R$^3$ form a benzoannellated ring;
each alkyl, cycloalkyl or alkenyl is unsubstituted or substituted with halogen or OH;
each aryl or benzoannellated ring is unsubstituted or substituted with halogen, OH or C$_1$-C$_4$alkyl;
and
a compound of formula

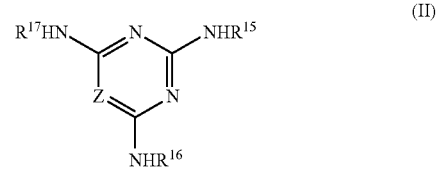

or a tautomeric form thereof, wherein
Z is N or CR$^{18}$;
R$^{18}$ is hydrogen, C$_1$-C$_8$alkyl, C$_2$-C$_8$alkenyl, C$_6$-C$_{10}$aryl or C$_7$-C$_{10}$aralkyl;

$R^{15}$, $R^{16}$ and $R^{17}$ are independently of each other hydrogen, $C_1$-$C_8$alkyl, $C_6$-$C_{10}$aryl, $C_7$-$C_{10}$aralkyl or a group of formula

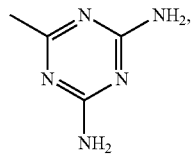
(III)

each alkyl or alkenyl is unsubstituted or substituted with halogen or OH,
each aryl is unsubstituted or substituted with halogen, OH or $C_1$-$C_4$alkyl;
or
(b2) an adduct containing a compound of formula

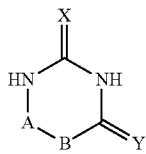
(I)

or a tautomeric form thereof, wherein
X is O, S or $NR^1$, preferably X is O or S;
Y is O, S or $NR^1$;
-A-B— is selected from the group consisting of —$CR^2$=$CR^3$—, —$CR^4R^5$—$CR^6R^7$—, —CY—$CR^8R^9$—, —CX—$NR^{10}$—, —$CR^{11}$=N—, —$CR^{12}R^{13}$—$NR^{14}$— and

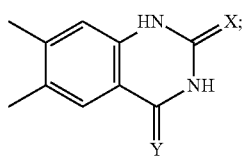

$R^1$ is hydrogen, $C_1$-$C_8$alkyl, $C_3$-$C_7$cycloalkyl, $C_6$-$C_{10}$aryl or $C_7$-$C_{10}$aralkyl;
$R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, halogen, $C_1$-$C_8$alkyl, $C_2$-$C_8$alkenyl or $C_6$-$C_{10}$aryl, or
$R^2$ and $R^3$ form a benzoannellated ring;
said alkyl, cycloalkyl or alkenyl is unsubstituted or substituted with halogen or OH;
said aryl or benzoannellated ring is unsubstituted or substituted with halogen, OH or $C_1$-$C_4$alkyl;
or
(b3) an adduct containing a compound of formula

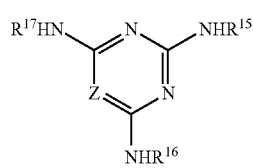
(II)

or a tautomeric form thereof, wherein
Z is N or $CR^{18}$;
$R^{18}$ is hydrogen, $C_1$-$C_8$alkyl, $C_2$-$C_8$alkenyl, $C_6$-$C_{10}$aryl or $C_7$-$C_{10}$aralkyl;
$R^{15}$, $R^{16}$ and $R^{17}$ are independently of each other hydrogen, $C_1$-$C_8$alkyl, $C_6$-$C_{10}$aryl, $C_7$-$C_{10}$aralkyl or a group of formula

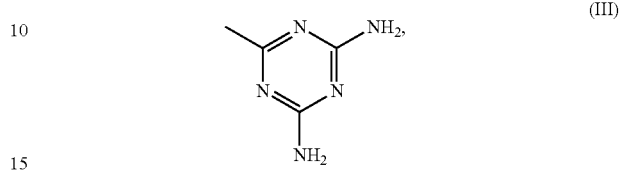
(III)

said alkyl or alkenyl is unsubstituted or substituted with halogen or OH, and said aryl is unsubstituted or substituted with halogen, OH or $C_1$-$C_4$alkyl;
wherein the organic pigment is selected from a diketopyrrolopyrrole, isoindoline, isoindolinone, phthalocyanine, quinacridone, quinophthalone, dioxazine pigment, or a mixture of said pigments.

A mixture of one or more organic pigments also includes a solid solution or a mixed crystal of pigments.

In a further aspect, the invention relates to a process for preparing the pigment composition, which process comprises treating (a) an organic pigment with an adduct (b) selected from an adduct (b1), (b2) or (b3), and to the pigment composition, obtainable by said process.

In a further aspect, the invention relates to the use of said pigment composition for coloring a coating composition, a paint, a printing ink, a liquid ink, plastics, a film or a fiber; and to a coating composition, a paint, a printing ink, a liquid ink, plastics, a film or a fiber, which is colored with said pigment composition.

The term "adduct" used herein means a hydrogen-bonded, stabilized adduct, in particular an approximately two-dimensional network of compounds formed by intermolecular hydrogen bonds. The adduct (b) containing a compound of formula (I) or a tautomeric form thereof, and/or a compound of formula (II) or a tautomeric form thereof means an adduct which may be formed by
  a compound of formula (I) or a tautomeric form thereof, and/or a compound of formula (II) or a tautomeric form thereof (adduct (b1)); or
  a compound of formula (I) or a tautomeric form thereof, and optionally a further compound different from a compound of formula (I) or (II) (adduct (b2)); or
  a compound of formula (II) or a tautomeric form thereof, and optionally a further compound different from a compound of formula (I) or (II) (adduct (b3)).

The terms "a", "an", "the", "at least one", and "one or more" are used interchangeably. Thus, for example, an adduct containing "a" compound of formula (I) means that the adduct include "one or more" compounds of formula (I).

The term "pigment composition" used herein means a composition comprising an organic pigment and a hydrogen-bonded, stabilized adduct (b) containing a compound of formula (I) and/or a compound of formula (II), wherein said adduct is associated onto the surface of the pigment and/or at least partially intercalated within the chromophore of the pigment, for example, by π-π stacking, hydrogen bonding and/or Van-der-Waals-forces. The pigment composition generally differs from a physically mixed blend of component (a) and (b).

The term "associated" or "modified" used herein in connection with the pigment composition means an interaction between the adduct and the chromophore of the pigment which is non-covalent and non-ionic.

The compound of formula (I) and compound of formula (II) also includes the corresponding tautomeric form.

Alkyl, e.g., $C_1$-$C_8$alkyl, $C_1$-$C_4$alkyl or $C_1$-$C_6$alkyl, may be within the given limits of carbon atoms linear or branched, where possible. Examples are methyl (Me), ethyl (Et), n-propyl, isopropyl, n-butyl, s-butyl, isobutyl, t-butyl, n-pentyl, 2-pentyl, 3-pentyl, 2,2-dimethylpropyl, n-hexyl, 1-methylhexyl, n-heptyl, isoheptyl, 1,1,3,3-tetramethylbutyl, 1-methylheptyl, 3-methylheptyl, n-octyl or 2-ethylhexyl. Each alkyl may be unsubstituted or substituted one or more times with OH or Hal.

Alkylene, e.g., $C_1$-$C_8$alkylene, $C_1$-$C_6$alkylene, or $C_1$-$C_4$alkylene, may be derived from above-defined alkyl by abstracting a hydrogen atom from any terminal carbon atom of the alkyl. Examples are methylene, ethylene, n-, isopropylene, n-, iso-, s-, t-butylene, n-pentylene, n-hexylene, n-heptylene or n-octylene. Said alkylene group may contain one or more groups selected from —O—, —S—, —$NR^{20}$—, phenyl, naphthyl or cyclohexylene, for example 1,4-phenylene, 1,4-naphthylene, 1,5-naphthylene, 2,6-naphthylene or 1,4-cyclohexylene. Preferably, the alkylene group is not interrupted or interrupted by one group. Where the alkylene group contains phenyl, naphthyl or cyclohexylene, these groups may be present at one end or within the chain.

Alkenyl, e.g., $C_2$-$C_8$alkenyl, $C_3$-$C_8$alkenyl, $C_3$-$C_6$alkenyl or $C_3$-$C_4$alkenyl, may be within the given limits of carbon atoms straight-chain or branched, where possible. Examples are vinyl, allyl, methallyl, isopropenyl, 2-butenyl, 3-butenyl, isobutenyl, n-penta-2,4-dienyl, or 3-methyl-but-2-enyl. The term "alkenyl" also comprises residues with more than one double bond that may be conjugated or non-conjugated, for example, may comprise one double bond. Each alkenyl may be unsubstituted or substituted one or more times with OH or Hal. Alkenylene, e.g., $C_2$-$C_8$alkenylene or $C_2$-$C_4$alkylene, may be derived from above-defined alkenyl by abstracting a hydrogen atom from any terminal carbon atom of the alkenyl.

Cycloalkyl, e.g., $C_3$-$C_7$cycloalkyl or $C_5$-$C_7$cycloalkyl, may be within the given limits of carbon atoms cyclopropyl, cyclobutyl, cyclopentyl, cyclohexyl, cycloheptyl, methylcyclopentyl, dimethylcyclopentyl or methylcyclohexyl, preferably cyclohexyl. Each cycloalkyl may be unsubstituted or substituted one or more times with OH or Hal. Cycloalkylene, e.g., $C_3$-$C_7$cycloalkylene, or $C_5$-$C_7$cycloalkylene, may be derived from above-defined cycloalkyl by abstracting a hydrogen atom from any carbon atom of the cycloalkyl. 1,4-Cyclohexylene is preferred.

Aryl, e.g., $C_6$-$C_{10}$aryl, may be within the given limits of carbon atoms phenyl, 1-naphthyl or 2-naphthyl, preferably phenyl. Each aryl may be unsubstituted or substituted one or more times with Hal, OH or $C_1$-$C_4$alkyl. Arylene, e.g. $C_6$-$C_{10}$arylene, may be 1,4-phenylene, 1,4-naphthylene, 1,5-naphthylene or 2,6-naphthylene, preferably p-phenylene.

Aralkyl, e.g., $C_7$-$C_{10}$aralkyl, may be within the given limits of carbon atoms benzyl, 2-benzyl-2-propyl, β-phenylethyl (phenethyl), α,α-dimethylbenzyl or ω-phenylbutyl, wherein both the aliphatic and the aromatic hydrocarbon group may be unsubstituted or substituted. The aromatic part may be substituted one or more times with Hal, OH or $C_1$-$C_4$alkyl; the aliphatic part may be substituted with OH or Hal. Preferred examples are benzyl or phenethyl.

Halogen (Hal) denotes I, Br, Cl, or F, preferably F or Cl on alkyl and Cl or Br on aryl.

The term "substituted" means "substituted one or more times with", that is 1 to 3 times, where possible, preferably 1 or 2 times, more preferably 1. If a substituent occurs more than once in a group, it may be different in each occurrence.

Of particular interest is a pigment composition containing (a) an organic pigment and an adduct (b1), as described herein-before.

Component (a) may be any organic pigment, especially a chromatic polycyclic organic pigment. The organic pigment is selected from a diketopyrrolopyrrole, dioxazine, isoindoline, isoindolinone, perylene, phthalocyanine, quinacridone, quinophthalone pigment, or a mixture of said pigments, including a solid solution or a mixed crystal.

Suitable examples include the following:

Quinacridone pigments: C.I. Pigment Orange 48 and 49; C.I. Pigment Red 122, 202, 206 and 209; C.I. Pigment Violet 19;

Quinophthalone pigments: C.I. Pigment Yellow 138;

Diketopyrrolopyrrole (DPP) pigments: C.I. Pigment Orange 71, 73 and 81; C.I. Pigment Red 254, 255, 264, 270 and 272;

Dioxazine pigments: C.I. Pigment Violet 23 and 37;

Isoindoline pigments: C.I. Pigment Yellow 139 and 185; C.I. Pigment Orange 61 and 69, C.I. Pigment Red 260;

Isoindolinone pigments: C.I. Pigment Yellow 109, 110 and 173;

Perylene pigments: C.I. Pigment Red 123, 149, 178, 179 and 224; C.I. Pigment Violet 29; and Phthalocyanine pigments: C.I. Pigment Blue 15, 15:1, 15:2, 15:3, 15:4, 15:6, 16; C.I. Pigment Green 7, 36.

Preferred pigments are Pigment Yellow 139, Pigment Orange 73, Pigment Red 122, Pigment Red 255, Pigment Violet 19, Pigment Violet 23, Pigment Violet 37 and Pigment Blue 15.3.

A suitable adduct of component (b) may also be formed by the compound of formula (II) and any dicarboxylic acid.

Accordingly, in a preferred embodiment, the pigment composition comprises (b3) the adduct containing the compound of formula (II), as defined in any aspect herein, or a tautomeric form thereof, and a compound of formula HOOC—$R^{19}$—COOH (IV), wherein $R^{19}$ is a direct bond, $C_1$-$C_8$alkylene, $C_2$-$C_8$alkenylene, $C_3$-$C_7$cycloalkylene or $C_6$-$C_{10}$arylene;

said alkylene, cycloalkylene or alkenylene is unsubstituted or substituted with halogen or OH, and said alkylene may further be interrupted by O, S, $NR^{20}$, phenyl, naphthyl or cyclohexylene, said arylene is unsubstituted or substituted with halogen, OH or $C_1$-$C_4$alkyl; and $R^{20}$ is hydrogen or $C_1$-$C_4$alkyl.

Preferably, $R^{19}$ is a direct bond, $C_1$-$C_6$alkylene, $C_2$-$C_4$alkenylene, cyclohexylene or $C_6$-$C_{10}$arylene; said groups are especially unsubstituted or substituted with OH, in particular a direct bond or $C_1$-$C_4$alkylene.

Suitable examples may be oxalic acid, malonic acid, succinic acid, glutaric acid, adipic acid, pimelic acid, and octanedioic acid, maleic acid, fumaric acid, tartraric acid and terephthalic acid, especially oxalic acid, malonic acid, succinic acid, glutaric acid, adipic acid, tartraric acid and terephthalic acid.

In a preferred aspect, the adduct (b) is selected from an adduct containing a compound of formula (I) (adduct (b2)), or a compound of formula (I) and a compound of formula (II) (adduct (b1)), or a compound of formula (II) and a compound of formula (IV) (adduct (b3)), each compound as described in any aspect herein.

The compound of formula (I) may include one or more compounds of formula (I), preferably one compound of formula (I). Accordingly, the same applies to the compound of formula (II) or (IV).

A preferred compound of formula (I) is of formula (I), wherein X and Y are O; X and Y are S; X is S and Y is O; X is NH and Y is O; or X is O and Y is NH; more preferably X and Y are O.

A further preferred compound of formula (I) is of formula (I), wherein the group -A-B— is selected from the group consisting of —CR$^2$=CR$^3$—, —CR$^4$R$^5$—CR$^6$R$^7$—, —CY—CR$^8$R$^9$—, —CX—NR$^{10}$—, —CR$^{11}$=N—, —CR$^{12}$R$^{13}$—NR$^{14}$— and

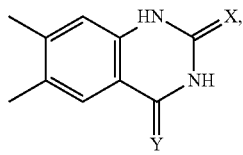

wherein R$^2$, R$^3$, R$^4$, R$^5$, R$^6$, R$^7$, R$^8$, R$^9$, R$^{10}$, R$^{11}$, R$^{12}$, R$^{13}$ and R$^{14}$ are independently of each other hydrogen, halogen, C$_1$-C$_4$alkyl, C$_3$-C$_4$alkenyl or C$_6$-C$_{10}$aryl, more preferably hydrogen, methyl, ethyl or phenyl; or
R$^2$ and R$^3$ form a benzoannellated ring.

Preferably, —CR$^2$=CR$^3$— is a group, wherein R$^2$ and R$^3$ are independently of each other H, methyl, ethyl, F, Cl, Br, or I; or R$^2$ and R$^3$ form a benzoannellated ring. Suitable groups of —CR$^2$=CR$^3$— are selected from —CH=CH—, —C(Me)=C(Et)-, —C(Et)=C(Me)-, —C(Hal)=CH— or

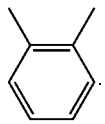

Further preferably, —CR$^4$R$^5$—CR$^6$R$^7$— is a group, wherein R$^4$, R$^5$, R$^6$ and R$^7$ are independently of each other H, methyl, ethyl, F, Cl, Br, or I. Suitable groups of —CR$^4$R$^5$—CR$^6$R$^7$— are selected from —CH$_2$—CH$_2$—, —CH(Me)-CH$_2$— or —CH(Et)-CH$_2$—.

Further preferably, —CY—CR$^8$R$^9$— is a group, wherein Y is O or NH; and R$^8$ and R$^9$ are independently of each other H, C$_1$-C$_6$alkyl, C$_3$-C$_4$alkenyl, benzyl or phenyl, especially H, methyl, ethyl, isopropyl, allyl, benzyl or phenyl. Suitable groups are —CO—CH$_2$—, —CO—C(Me)$_2$-, —CO—C(Et)$_2$-, —CO—CH(Me)-, —CO—CH(Et)-, —CO—C(Me)(Ph)-, —CO—C(Et)(Ph)-, —CO—CBr$_2$— or —C(NH)—CH$_2$—.

Further preferably, —CX—NR$^{10}$— is a group, wherein X is O; and R$^{10}$ is H or C$_1$-C$_6$alkyl, more preferably H, methyl, ethyl, isopropyl, n-butyl or isobutyl.

Further preferably, —CR$^{11}$=N— is a group, wherein R$^{11}$ is H, methyl or ethyl, especially H.

Further preferably, —CR$^{12}$R$^{13}$—NR$^{14}$— is a group, wherein R$^{12}$, R$^{13}$ and R$^{14}$ are independently of each other H, methyl or ethyl, especially H.

Especially suitable compounds of formula (I) are selected from

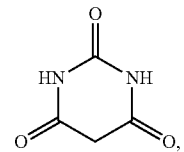 (Ia)

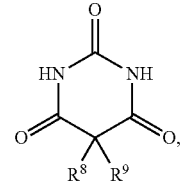 (Ib)

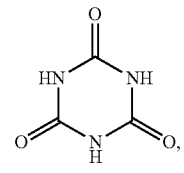 (Ic)

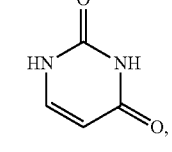 (Id)

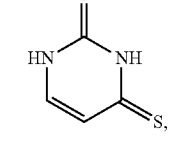 (Ie)

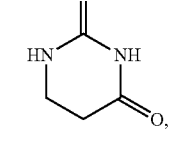 (If)

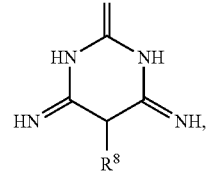 (If)

wherein R$^8$ is H, methyl, ethyl, isopropyl, allyl, benzyl or phenyl, or

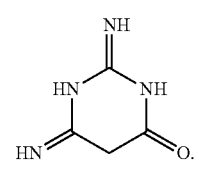 (Ig)

A preferred compound of formula (II) is of formula (II), wherein Z is N or CR$^{18}$, wherein R$^{18}$ is hydrogen, C$_1$-C$_4$alkyl or phenyl, more preferably hydrogen, methyl, ethyl or phenyl; and $R^{15}$, $R^{16}$ and $R^{17}$ are independently of each other hydrogen, $C_1$-$C_6$alkyl, phenyl, 1-naphthyl, benzyl or a group of formula

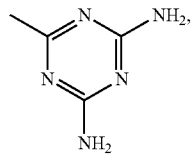

said phenyl or naphthyl is unsubstituted or substituted with Cl, Br, I, methyl or ethyl; more preferably $R^{15}$ is hydrogen, and $R^{16}$ and $R^{17}$ are the same and are $C_1$-$C_4$alkyl or phenyl, wherein said phenyl is optionally substituted.

Especially suitable compounds of formula (II) are selected from

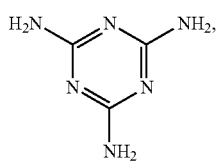

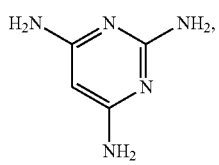

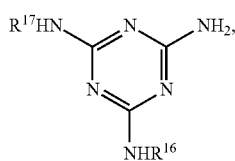

wherein $R^{16}$ and $R^{17}$ are $C_1$-$C_4$alkyl or phenyl, or

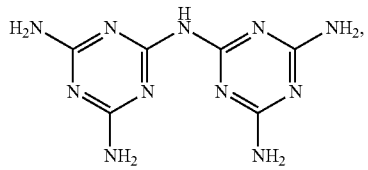

Accordingly, in a preferred embodiment, the pigment composition comprises (b1) the adduct containing the compound of formula (I) or a tautomeric form thereof, wherein X and Y are O; -A-B— is —CY—CR$^8$R$^9$— or —CX—NR$^{10}$—;
$R^8$, $R^9$ and $R^{10}$ are hydrogen; and
the compound of formula (II) or a tautomeric form thereof, wherein
Z is N; and $R^{15}$, $R^{16}$ and $R^{17}$ are independently of each other hydrogen or $C_1$-$C_4$alkyl.

In a further preferred embodiment, the pigment composition comprises
(b1) the adduct containing the compound of formula (I) or a tautomeric form thereof, wherein X and Y are O; -A-B— is —CY—CR$^8$R$^9$— or —CX—NR$^{10}$—;
$R^8$, $R^9$ and $R^{10}$ are hydrogen; and
the compound of formula (II) or a tautomeric form thereof, wherein
Z is CR$^{18}$; $R^{18}$ is hydrogen, $C_1$-$C_4$alkyl, phenyl or $C_7$-$C_{10}$aralkyl; and
$R^{15}$, $R^{16}$ and $R^{17}$ are independently of each other hydrogen or $C_1$-$C_4$alkyl.

In a further preferred embodiment, the pigment composition comprises
(b1) the adduct containing the compound of formula (I) or a tautomeric form thereof,
wherein X and Y are O; -A-B— is —CY—CR$^8$R$^9$— or —CX—NR$^{10}$—;
$R^8$, $R^9$ and $R^{10}$ are hydrogen; and
the compound of formula (II) or a tautomeric form thereof, wherein
Z is N or CR$^{18}$; $R^{18}$ is hydrogen, $C_1$-$C_4$alkyl, phenyl or $C_7$-$C_{10}$aralkyl; and
$R^{15}$, $R^{16}$ and $R^{17}$ are independently of each other hydrogen or $C_1$-$C_4$alkyl.

In a further preferred embodiment, the pigment composition comprises
(b1) the adduct containing the compound of formula (I) or a tautomeric form thereof, wherein X and Y are O; -A-B— is —CY—CR$^8$R$^9$— or —CX—NR$^{10}$—;
$R^8$, $R^9$ and $R^{10}$ are hydrogen; and
the compound of formula (II) or a tautomeric form thereof, wherein Z is N; and $R^{15}$, $R^{16}$ and $R^{17}$ are hydrogen.

In a further preferred embodiment, the pigment composition comprises
(b1) the adduct containing the compound of formula (I) or a tautomeric form thereof, wherein X and Y are independently of each other O or NR$^1$; -A-B— is —CY—CR$^8$R$^9$—;
$R^1$, $R^8$, $R^9$ and $R^{10}$ are hydrogen; and
the compound of formula (II) or a tautomeric form thereof,
Z is N or CR$^{18}$; $R^{18}$ is hydrogen, $C_1$-$C_4$alkyl, phenyl or $C_7$-$C_{10}$aralkyl; and
$R^{15}$, $R^{16}$ and $R^{17}$ are independently of each other hydrogen or $C_1$-$C_4$alkyl.

A suitable adduct of component (b2) may also be formed by only a compound of formula (I), for example, by one or more compounds of formula (I), preferably by one compound of formula (I).

Accordingly, a preferred pigment composition contains the adduct (b2) which is formed of a compound of formula (I) or a tautomeric form thereof, wherein
X and Y are O;
-A-B— is selected from the group consisting of —CR$^2$=CR$^3$—, —CY—CR$^8$R$^9$— and —CX—NR$^{10}$—;
$R^2$, $R^3$ and $R^{10}$ are hydrogen; and
$R^8$ and $R^9$ are independently of each other hydrogen, halogen or $C_1$-$C_4$alkyl.

Also preferred is a pigment composition containing the adduct (b2) which is formed of a compound of formula (I) or a tautomeric form thereof, wherein
X and Y are independently of each other O or NR$^1$;
-A-B— is selected from the group consisting of —CR$^2$=CR$^3$—, —CY—CR$^8$R$^9$— and —CX—NR$^{10}$—;
$R^1$, $R^2$, $R^3$ and $R^{10}$ are hydrogen; and
$R^8$ and $R^9$ are independently of each other hydrogen, halogen or $C_1$-$C_4$alkyl.

More preferred is a pigment composition, wherein the adduct (b2) is formed of a compound of formula (I) or a tautomeric form thereof, wherein X and Y are O, -A-B— is selected from the group consisting of —CY—CR$^8$R$^9$— and —CX—NR$^{10}$—; R$^8$, R$^9$ and R$^{10}$ are hydrogen.

Especially preferred examples for forming the adduct are of formula (Ia), (Ib), (Ic) or (If), in particular (Ia) or (Ib).

A further suitable adduct of component (b) may also be formed by only a compound of formula (II), preferably by a compound of formula (IIa). However, this embodiment is less preferred.

Especially preferred adducts are formed by
a compound of formula (Ia) and a compound of formula (IIa); or
a compound of formula (Ia) and a compound of formula (IIb); or
a compound of formula (Ib) and a compound of formula (IIa); or
a compound of formula (Ib) and a compound of formula (IIb); or
a compound of formula (Ia); or
a compound of formula (Ib).

Advantageously, the adduct is formed of only one compound or of two different compounds. Thus, the adduct preferably consists essentially of a compound of formula (I) or a compound of formula (II). Alternatively, the adduct is preferably a mixed adduct consisting essentially of a compound of formula (I) and a compound of formula (II), or a compound of formula (II) and a compound of formula (IV). This means that the adduct may only contain other substances in an amount of 0 to 5 wt %, based on the total weight of component (b), preferably 0 to 3% by weight.

A mixture of more than one adduct described herein may also be used to form a pigment composition of the invention.

In principle, any adduct described as solid-state structures based on secondary diamides by J. C. MacDonald and G. M. Whitesides in Chem. Rev. 94 (1994) 2383-2420 may be used in the instant invention. The compounds of formula (I), (II) or (IV) are, for example, commercially available or may be synthesized by general methods known in the art, for example, as disclosed in the references cited in Chem. Rev. 94 (1994) 2383-2420.

In a further aspect, the invention relates to a process for preparing a pigment composition, as defined in any aspect herein-before, which process comprises treating (a) an organic pigment with an adduct (b) selected from an adduct (b1), (b2) or (b3).

As an organic pigment any crude pigment of the various classes may be used for preparing the pigment composition of the invention. The crude pigment may be obtained by any process known to one skilled in the art. The crude pigment may be used, as directly obtained after synthesis, as a wet cake or after isolating usually by filtering, washing and drying, dependent on the subsequent treating or finishing step. A wet cake may comprise 30 to 60% by weight of pigment, based on the total weight of the wet cake. Moreover, an already finished pigment may be used, for example, finished by commonly used methods for conditioning organic pigments. Alternatively, any commercially available organic pigment may be used.

Preferably, the crude pigment, as isolated by filtering, washing and drying, is used.

The adduct containing the compound of formula (I) and/or the compound of formula (II) may be prepared in situ during the treating step of the organic pigment (a) or may be prepared separately to be added to the organic pigment (a) to form the pigment composition.

In case the adduct is formed of two different compounds, e.g., a compound of formula (I) and a compound of formula (II), the adduct is suitably prepared prior to adding to the organic pigment (a). The adduct is suitably prepared by dissolving each compound separately in water followed by blending the solutions under stirring until a precipitate has been formed. Dissolving may be carried out at room temperature or at an elevated temperature, for example, up to 60° C. Blending the solutions may be carried out both at room temperature and at temperatures up to 60° C. to form the adduct as a precipitate. The precipitate is generally isolated by filtering and washing, usually with water. The adduct may be used after drying at temperatures of from 20 to 100° C., preferably 60 to 90° C. or as a wet cake dependent on the subsequent treating or finishing step of the organic pigment.

Usually, the mole ratio of compound of formula (I) to compound of formula (II) may be in the range of 0.4:0.6 to 0.7 to 0.3, preferably about 0.45:0.55 to 0.70:0.30, more preferably 0.45:0.55 to 0.55:0.45. Most preferably, the mole ratio is about 1:1.

Usually, the mole ratio of compound of formula (II) to compound of formula (IV) may be in the range of 0.4:0.6 to 0.7:0.3, preferably about 0.45:0.55 to 0.70:0.30, more preferably 0.45:0.55 to 0.55:0.45. Most preferably, the mole ratio is about 1:1.

The process for preparing the instant pigment composition may be performed by subjecting a blend of the organic pigment (a) and the adduct containing the compound of formula (I) and/or the compound of formula (II) as such to a comminution step or a dispersing step, usually involving high energy including milling media.

Accordingly, in a preferred aspect, the invention relates to a process, wherein the organic pigment (a) is treated with the adduct (b) using salt kneading, wet milling or dispersing, preferably with high energy including milling media, wherein optionally the adduct (b) is prepared in situ during the treating step.

The weight ratio of organic pigment (component (a)) to the adduct used for preparing the pigment composition of the present invention (component (b)) may be in the range of from 0.85:0.15 to 0.5:0.5, preferably 0.80:0.2 to 0.65:0.35. The weight ratio used for the process of preparation usually corresponds to the weight ratio of the pigment composition of the invention. In case the adduct is prepared in situ the compounds forming the adduct of component (b) may be suitably added in excess up to 20% by weight, based on the organic pigment (a), preferably up to 10% by weight. The compounds not forming an adduct may easily be separated by washing. The amount of the adduct present in the pigment composition of the invention may be calculated, for example, by weighing of the dried pigment (corresponding to the yield) or determined by elemental analysis.

Preferably, the comminution step may be carried out by salt kneading or wet milling.

Salt kneading may be carried out in the presence of an inorganic salt or a salt of an organic acid and an organic liquid in which the pigment, adduct and inorganic salt or salt of an organic acid are substantially insoluble. Any kneader for salt kneading known in the art may be used, for example, common double-shaft kneaders, such as Z-blade kneaders, planetary kneaders or screw kneaders, but also single-shaft kneaders, high speed mixers or extruders are likewise possible. The organic pigment (a) and the adduct are preferably used in dried form, each having residual amounts of liquids of up to 5% by weight, based on the pigment and adduct, respectively.

Suitable salts for salt kneading are water-soluble salts having a solubility of at least 10 g/100 ml in water. Suitable examples are sodium chloride, potassium chloride, calcium chloride, zinc chloride, aluminum chloride, sodium sulfate, aluminum sulfate, calcium carbonate, sodium acetate, calcium acetate, sodium citrate, potassium sodium tartrate and the like, with or without water of crystallization. Preferred inorganic salts are sodium chloride and sodium sulfate, more preferably sodium chloride. Typically, technical-grade salts with or without preceding micronization are used. The salts preferably have an average particle size of from 5 to 200 µm, more preferably from 10 to 50 µm. In addition, they appropriately only have a solubility of ≤100 mg/l, in particular ≤10 mg/l (in each case at 20° C.), in the organic solvent; they are preferably virtually insoluble therein.

Suitable liquids for use in salt kneading are liquids, preferably organic solvents or low low-melting solids that liquefy during grinding, in which the organic pigment and salt are substantially insoluble but which enable the physical transformation of the crude pigment to the instant pigment composition. Examples of organic solvents are alcohols, such as methanol, ethanol, (di, tri)ethylene glycol, (di)propylene glycol, or glycerol; lower organic acids, such as formic or acetic acid; ethers such as dioxane, tetrahydrofuran, ethylene glycol monoethyl or diethyl ether, ethylene glycol monobutylether, or oligo- and polyglycol ethers; ketones such as acetone, diacetone alcohol, cyclohexanone or methyl ethyl ketone, aromatics, such as toluene, xylene, chlorobenzene, nitrobenzene, or chloronaphthalene; esters such as butyl acetate, glycerol triacetate, methyl benzoate, dimethylphthalate or methyl salicylate; amides, such as dimethylformamide, dimethylacetamide or N-methylpyrrolidone; sulfones such as sulfolane or sulfoxides such as dimethyl sulfoxide. Particularly suitable solvents are diethylene glycol, triethylene glycol or diacetone alcohol.

In general, the kneading mass contains, per g of the total mass of organic pigment (a) and adduct, or organic pigment (a) and compound(s) forming the adduct of component (b) in situ, from 1 to 15 g, preferably from 2 to 8 g of inorganic salt or salt of an organic acid, and from 0.3 to 2 g, preferably from 0.5 to 2 g, of organic liquid.

The kneading temperature is generally of from 20 to 150° C., preferably 30 to 110° C., more preferably 30 to 90° C.

The salt kneading step should be carried out for a sufficient period of time to allow the particles to attain optimum stability, pigmentary size and distribution. The period of time is not critical and may range from 2 to 15 hours, preferably 2 to 10 hours, in particular from 2 to 6 hours.

The speed or rotation rate is appropriately selected in such a way that the kneading mass is moved homogeneously and with uniform shear.

The product resulting after kneading may be stirred and granulated in water to remove salt and organic liquid and isolated by common methods, like filtering, washing usually salt free with water and drying, preferably at a temperature of from 50 to 90° C.

Wet milling may be carried out in the presence of milling media and an aqueous medium, preferably water, in which the organic pigment and the adduct are substantially insoluble. Any milling apparatus may be used insofar as it permits temperature control and application of high shear. Suitable milling apparatus are pearl mills, ball mills, vibrator mills, sand mills, agitator mills, centrifugal vortex mills, attritors, and the like. Suitable milling media are, for example, steel balls, ceramic beads like silicon/aluminum/ zirconium oxide beads or yttrium stabilized zircon pearls, or glass beads typically having a diameter of from 0.2 to 3 mm, preferably 0.3 to 1.8 mm.

For safety reasons, it may be advantageous to carry out the milling under inert atmosphere.

Wet milling may preferably be carried out in an aqueous medium, preferably water. Suitable organic solvents for the aqueous medium are in principle the solvents mentioned for salt kneading, preferably water-miscible solvents.

The total amount of organic pigment (a) and adduct or the compound(s) forming the adduct of component (b) in the aqueous medium is advantageously of from 5 to 25% by weight, based on the total weight of the milled paste, preferably 5 to 15% by weight. Preferably, the organic pigment (a) is pre-dispersed in the aqueous medium, preferably water, to form a uniform aqueous dispersion, typically of from 0.5 to 2 hours, prior to the step of wet grinding. The adduct or the compound(s) forming the adduct of component (b) may be present during pre-dispersing or may be added after the organic pigment (a) has been pre-dispersed. The pre-dispersing step may be carried out in any suitable dispersing apparatus known in the art for dispersing pigments like any dissolvers or the like. Typically, dispersing is operated at a speed of from 800 to 3000 rpm dependent on the viscosity of the dispersion medium, usually without milling media.

The milling temperature is generally of from 10 to 100° C., preferably 20 to 80° C.

The speed or rotation rate is appropriately selected in such a way that the milling mass is moved homogeneously and with uniform shear. The milling step may be operated in a circulation or single/multi-pass procedure.

The milling step should be carried out for a sufficient period of time to allow the particles to attain optimum stability, pigmentary size and distribution, typically dependent on the mode of operation. The period of time is not critical and may range from 30 min to 15 hours, preferably 1 to 10 hours, in particular from 2 to 5 hours.

The product resulting after wet milling may be isolated by common methods, like filtering, washing usually with water and drying, preferably at a temperature of from 50 to 90° C.

If desired, the milled material obtained in the case of milling with steel balls may be subjected to an aftertreatment with hydrochloric acid to remove any iron attritus present.

Alternatively, the pigment composition of the invention may be obtained by conventional dry-milling or by a high energy powder grinding, for example, in a jet mill such as opposed fluidized jet mill.

Also preferably, the pigment composition may be prepared by dispersing the organic pigment (a) with the already formed adduct or the compound(s) forming the adduct of component (b). Dispersing may be carried out in an aqueous medium, preferably in water. Suitable organic solvents for the aqueous medium are in principle the solvents mentioned for salt kneading, preferably water-miscible solvents.

The dispersing step is generally carried out with any dispersing apparatus using milling media. Such dispersing differs from the usual pre-dispersing step for providing a homogenous dispersion.

Suitable dispersing apparatus may any dissolver or paint shaker known in the art for dispersing pigments. For example, a dissolver of the type DISPERMAT or a paint shaker of the type Skandex may be used. Typically, dispersing is operated at a speed of from 800 to 10,000 rpm, preferably 1000 to 3000 rpm, dependent on the viscosity of the dispersion medium. The dispersing step is carried out with any milling media, preferably with milling media like glass beads or ceramic beads typically having a diameter of from 0.3 to 2 mm, preferably 0.8 to 2 mm.

The total amount of organic pigment (a) and adduct or the compound(s) forming an adduct of component (b) in the aqueous medium is advantageously of from 5 to 25% by weight, based on the total weight of the dispersed paste, preferably 5 to 15% by weight.

Dispersing is usually carried out of from 10 to 100° C., preferably 20 to 80° C.

The speed or rotation rate is appropriately selected in such a way that the dispersing mass is moved homogeneously and with uniform shear.

The dispersing step should be carried out for a sufficient period of time to allow the particles to attain optimum stability, pigmentary size and distribution, typically dependent on the mode of operation. The period of time is not critical and may range from 30 min to 15 hours, preferably 1 to 10 hours, in particular from 2 to 7 hours.

The product resulting after dispersing may be isolated by common methods, like filtering, washing usually with water and drying, preferably at a temperature of from 50 to 90° C.

The pigment composition may be prepared by the processes, as described herein-before. Especially suitable is the process, wherein (a) the organic pigment is treated with an adduct (b) by salt kneading or wet milling, in particular by salt kneading. Optionally, the adduct (b) may be prepared in situ during the treating step.

In a further aspect, the invention relates to a pigment composition obtainable by the process, as defined herein-before. Accordingly, the invention relates to a pigment composition, as defined in any aspect herein-before, obtainable by a process, which process comprises treating (a) an organic pigment with an adduct (b) selected from an adduct (b1), (b2) or (b3).

The pigment composition of the invention may be used as solid systems of free-flowing, pulverulent consistency, as granules, or as aqueous presscake, preferably as powder or granules.

In order to control, for example, the crystal size it may be of advantage to carry out the process for preparing the instant pigment composition in the presence of a pigment synergist, in which case the pigment is used typically in an amount of from 0.01 to 0.1 g of synergist per gram of organic pigment (a) is used. The pigment synergist may be added at any stage of the preparation process as well as in the course of synthesis of the crude pigment. The pigment composition may also only be mixed with the pigment synergists for the application.

Pigment synergists are compounds which contain some or all of the pigment chromophore in their molecular structure and preferably have acidic or basic groups, for example, aminomethyl, sulpho, carboxyl, amidosulphonyl or amidocarbonyl groups. The structure of the pigment system does not have to coincide with the structure of the organic pigment (a). Examples of suitable pigment synergists are copper phthalocyanine derivatives such as Solsperse® 5000 or 12000 (Lubrizol Corp., USA), or BYK's synergist 2100, or azo derivatives such as Solsperse 22000 and Synergist 2105. Further suitable examples are pyrazole-containing pigment derivatives, for example, as disclosed in EP-A-0485337, or quinophthalone derivatives, for example, as described in US-A-2003/0172847; perylene based pigment derivatives, for example, as disclosed, in US-A-2007/0151478 or US-A-2004/0215015, and derivatives, as disclosed, for example, in WO-A-02/10288 or WO-A-2009/144115.

The presence of pigment synergists often has a positive effect on the dispersibility and the flocculation stability of the instant pigment composition in the application medium and thus on the rheology of the application medium, for example, of a paint system.

The pigment composition of the invention may be after-treated by common methods such as contacting with suitable additives such as surfactants, dispersants, resins, waxes, fillers, defoamers, antidust agents, extenders, shading colorants, preservatives, dryness retarders, rheology control additives, wetting agents, antioxidants, UV absorbers, light stabilizers or combinations thereof. Suitably, an after-treatment by rosination may be performed.

Such an after-treatment may also be omitted entirely.

Preferably, the pigment composition of the invention consists essentially of components (a) and (b). The amount of optional components like the above-mentioned additives and pigment synergists may be of from 0 to 20% by weight, based on the total weight of the pigment composition, preferably 0 to 10% by weight, more preferably 0 to 5% by weight.

The pigment composition of the invention may also be used in form of a pigment preparation, as disclosed, for example, in EP-A-902061 or EP-A-1474484.

The pigment composition of the invention is outstandingly suitable for all pigment end-use applications, especially coloring high molecular weight organic or inorganic materials of natural and synthetic origin, for example, a) for mass coloring polymers, e.g. in the form of resins, rubber or plastics including films and fibers;

b) for the preparation of paints, paint systems, coating compositions, for example, in automotive and industrial coating compositions, c) liquid and printing inks, e.g. digital printing like ink-jet printing, as well as for toners in electrophotography, e.g. for laser printers;

d) as an additive to colorants, such as pigments and dyes; and the like.

Paints are aqueous or solvent borne coating materials and also powder coating materials, in which the pigment composition of the invention may be employed alone or in combination with extenders, white pigments, chromatic pigments or black pigments. Organic film-forming binders that may be used include all of the binders that are usual in the coatings sector. Examples of binder materials which may be colored with the pigment composition of the invention include more particularly:

oil-based materials (based on linseed oil or polyurethane oils), cellulose-based materials (NC, CAB, CAP), materials based on chlorinated rubber, vinyl materials (based on PVC, PVDF, VC copolymer, polyvinyl acetate, polyvinyl ester dispersion, polyvinyl alcohol, polyvinyl acetal, polyvinyl ether, polystyrene, styrene copolymers), acrylic materials, alkyd materials, saturated polyester materials, unsaturated polyester materials, polyurethane materials (one pack, two pack), epoxy materials, silicone materials.

The systems are described in detail in D. Stoye, W. Freitag, Paints, Coatings and Solvents, Second Edition, 1998, Wiley-VCH.

Combinations with effect pigments are also possible and lead to special effects. Effect pigments include platelet-shaped metallic and/or oxidic effect pigments, generally known in the art.

Preferably, the pigment composition is used in waterborne and solvent borne coating applications, more preferably in decorative coating compositions like architectural, automotive or industrial coating compositions.

Also preferably, the pigment composition is used in waterborne and solvent borne printing inks based on various binder materials, as mentioned herein-before for coating applications, preferably for ink-jet printing.

The pigment composition of the invention may also advantageously be used to color customary plastics and blends of plastics, either as pigment composition alone or in combination with white, chromatic, and black pigments, and in combination with all typical additives and stabilizers. Plastics may be in form of powder, plastic masses, melts or in form of spinning solutions. Suitable plastics include polyolefins, unplasticized and plasticized polyvinyl chloride (PVC), and also all engineering plastics such as acrylonitrile/butadiene/styrene copolymers (ABS), polystyrene, polyamide, polyester, polycarbonate, polyetherketone, and also polyurethanes and rubber systems. Preferred plastics are polyolefins and polyamides.

The pigment composition may be incorporated into various application media by techniques common in the art.

The pigment composition may be used in an amount of from 0.01 to 75% by weight, preferably 0.01 to 50% by weight, based on the total weight of the material to be colored.

In a further aspect, the invention relates to the use of a pigment composition, as defined in any aspect herein-before for coloring or pigmenting a coating composition, a paint, a printing ink, a liquid ink, plastics, a film or a fiber. The coating composition may be any decorative coating composition like automotive, architectural or industrial coating composition or a paint, especially a waterborne or a solvent borne coating composition. Preferably, the pigment composition is used as a colorant for an automotive, architectural, industrial coating composition, a paint, a printing ink or plastics.

In a further aspect, the invention relates to a coating composition, a paint, a printing ink, a liquid ink, plastics, a film or a fiber, which is colored or pigmented with a pigment composition, as defined in any aspect herein-before.

In a further aspect, the invention relates to a process for coloring or pigmenting a coating composition, paint, a printing ink, a liquid ink, plastics, a film or a fiber, which process comprises adding thereto a pigment composition, as defined in any aspect herein-before.

The pigment compositions of the invention are excellent in their coloristic properties, in particular in chroma and transparency. The efficiency of finishing the organic pigment (a) is highly improved. The color strength may be maintained or is improved, dependent on the desired application. The instant pigment compositions show significantly improved chroma values compared to a pigment (a) of the same Color Index without modifying with an adduct of component (b) or compared to a physical blend of the components (a) and (b), needing significantly less of coloring component (a). Especially, the color strength can be approximately maintained or even improved.

Further, the pigment compositions of the invention are excellent in their chemical resistance, in particular in their alkali resistance, wherein the other coloristic and performance properties are not adversely affected.

The pigment compositions of the invention are excellent in their thermal stability in plastics, especially in polyolefin or polyamide plastics.

The pigment composition has a significantly reduced amount of organic pigment (a) compared to another finished organic pigment (a) of the same Color Index. Thus, the instant invention allows providing a pigment composition which reduces costs in preparation and which have similar or even higher color strength and significantly higher chroma. No further finishing step is generally required. A desired color strength may be adapted with a significantly reduced amount of pigment (a).

Further, the pigment compositions, especially based on dioxazine pigments, like Pigment Violet 23 and 37, or phthalocyanine pigments, like Pigment Blue 15.1, 15.2, 15.3, 15.4, or 15.6, show improved stability against oxidative conditions. No visible change in color may be recognized.

Accordingly, in a further aspect, the invention relates to the use of an adduct (b), as defined in any aspect herein-before, for enhancing the oxidation stability of an organic pigment (a), preferably a dioxazine or a phthalocyanine pigment (a), preferably in an application in a high molecular weight organic material. A dioxazine pigment is most preferred, for example, Pigment Violet 23 or Pigment Violet 37

The definitions and preferences given for the pigment mentioned herein-before apply in any combination as well as in any combination for the other aspects of the invention.

The present invention will now be explained in more detail with reference to the following examples. These examples should not be construed as limited. Unless otherwise stated, "%" is always % by weight.

EXAMPLES

To determine the CIELAB values of hue h [°], chroma C* and lightness L*, the coating films obtained (in masstone) are measured using a Minolta Spectrophotometer CM-3610d. Evaluation takes place on the data obtained at a measurement angle of 45°. The color strength is determined in white reduction.

Example 1 a) 60 g of melamine (2,4,6-triamino-1,3,5-triazine) are dissolved at 45° C. in 600 ml of water (solution A). 60 g of barbituric acid (pyrimidine-2,4,6-trione) are dissolved at 45° C. in 1000 ml of water (solution B). Solution A is slowly added to solution B under stirring. The precipitate of the formed 1:1 adduct of melamine and barbituric acid is isolated by filtration and dried at 60° C. in a vacuum oven.

b) 37 g of Pigment Red 255 (crude pigment) and 30 g of the precipitate of step a) are blended with 470 g of sodium chloride (milled grade) and 140 g of diacetone alcohol and kneaded in a 1 L Z-blade kneader (Meili) for 7 hours at 35° C. The resulting paste is then dispersed in 3 l of water, the product is isolated by filtration, washed salt-free with water and dried in a vacuum oven overnight at 80° C.

c) The procedure of b) is repeated with the exception that 15 g of melamine and 15 g of barbituric acid are used instead of 30 g of the precipitate of step a).

d) The procedure of Example b) is repeated with the exception that 30 g of a 1:1 adduct of melamine and succinic acid (mole ratio; prepared in analogy to Example a) is used instead of the precipitate of step a).

Comparative Example 1a

Irgazin Red L 3551 HD applied with the corresponding amount of the pigment composition (67 g).

Comparative Example 1b

Example 1 b is repeated with the exception that 67 g of crude Pigment Red 255 is used instead of 37 g of crude pigment and 30 g of precipitate of step a).

The coloristic data are listed in Tables 1a-c.

Example 2 a) Example 1a) is repeated.

b) 71 g of Pigment Orange 73 (crude pigment) and 30.4 g of the precipitate of step a) are blended with 428 g of sodium chloride (milled grade) and 154 g of diacetone alcohol and kneaded in a 1 l Z-blade kneader (Meili) for 6 hours at 40° C. The resulting paste is then dispersed in 3 l of water, the product is isolated by filtration, washed salt-free with water and dried in a vacuum oven overnight at 80° C.

Comparative Example 2

Irgazin Orange L 2990 HD applied with the corresponding amount of the pigment composition (101.4 g).

The coloristic data are listed in Table 2.

Example 3 a) Example 1a) is repeated.

b) 71 g of Pigment Violet 37 (crude of Cromophtal Violet D 5700) and 30.4 g of the precipitate of step a) are blended with 428 g of sodium chloride (milled grade) and 150 g of diacetone alcohol and kneaded in a 1 l Z-blade kneader (Meili) for 6 hours at 40° C. The resulting paste is then dispersed in 3 l of water, the product is isolated by filtration, washed salt-free with water and dried in a vacuum oven overnight at 80° C.

Comparative Example 3

Cromophtal Violet D 5700 applied with the corresponding amount of the pigment composition (101.4 g).

The coloristic data are listed in Tables 3a and 3b.

Example 4 a) Example 1a) is repeated.

b) 71 g of Pigment Violet 19 (crude pigment) and 30.4 g of the precipitate of step a) are blended with 428 g of sodium chloride (milled grade) and 154 g of diacetone alcohol and kneaded in a 1 l Z-blade kneader (Meili) for 6 hours at 40° C. The resulting paste is then dispersed in 3 l of water, the product is isolated by filtration, washed salt-free with water and dried in a vacuum oven overnight at 80° C.

Comparative Example 4

Cinquasia Red L 4100 HD (γ-quinacridone) applied with the corresponding amount of the pigment composition (101.4 g).

The coloristic data are listed in Table 4.

Example 5 a) Example 1a) is repeated.

b) 71 g of Pigment Blue 15.3 (crude pigment) and 30.4 g of the precipitate of step a) are blended with 428 g of sodium chloride (milled grade) and 150 g of diacetone alcohol and kneaded in a 1 l Z-blade kneader (Meili) for 6 hours at 40° C. The resulting paste is then dispersed in 3 l of water, the product is isolated by filtration, washed salt-free with water and dried in a vacuum oven overnight at 80° C.

Comparative Example 5

Heliogen Blue K 7090 applied with the corresponding amount of the pigment composition (101.4 g).

The coloristic data are listed in Tables 5a and 5b.

Example 6 a) Example 1a) is repeated.

b) 85 g of Pigment Yellow 139 (crude pigment) and 68.7 g of the precipitate of step a) are blended with 340 g of sodium chloride (milled grade) and 142 g of diacetone alcohol and kneaded in a 1 l Z-blade kneader (Meili) for 3 hours at 40° C. The resulting paste is then dispersed in 3 l of water, the product is isolated by filtration, washed salt-free with water and dried in a vacuum oven overnight at 80° C.

Example 7 a) 60 g of melamine (2,4,6-triamino-1,3,5-triazine) are dissolved at 45° C. in 1000 ml of water (solution a). 60 g of cyanuric acid (1,3,5-triazinetriol) are dissolved at 45° C. in 2000 ml of water (solution B). Solution A is slowly added to solution B under stirring. The precipitate of the 1:1 adduct of melamine and cyanuric acid is isolated by filtration and dried at 60° C. in a vacuum oven.

b) 85 g Pigment Yellow 139 (crude pigment) and 68.7 g of the precipitate of step a) are blended with 340 g of sodium chloride and 150 g (125 g from the beginning and 25 g are added during the kneading) of diacetone alcohol and kneaded in a 1 l Z-blade kneader for 3 hours at 40° C. The resulting paste is then dispersed in 3 l of water, the product is isolated by filtration, washed salt-free with water and dried in a vacuum oven overnight at 80° C.

Example 8

50 g of Pigment Yellow 139 (crude pigment) and 50 g of a 1:1 adduct of melamine and barbituric acid (prepared according to Example 1a) are dispersed in 450 g of water with a teeth-stirrer for 1 hour at 1000 rpm. A 400 ml glass WAB Willy A. Bachofen DynoMill KDL—equipped with two PU disks, 3000 rpm, filled with 250 ml of Yttrium stabilized Zirkonia pearls (ø 1.2-1.4 mm) is fed—through a peristaltic pump at a speed of 600 ml per min—with 400 ml of water followed by the pigment suspension. The suspension is milled for 3 hours at about 40° C. The product is isolated by filtration, washed with water and dried at 80° C. in a vacuum oven.

Example 9

The procedure of Example 8 is repeated with the exception that an adduct of melamine and cyanuric acid (prepared according to Example 7a) is used instead of an adduct of melamine and barbituric acid, and the weight ratio of Pigment Yellow 139 to adduct is of 55:45.

Example 10a 50 g of Pigment Yellow 139 (crude pigment) and 50 g of a 1:1 adduct of melamine and barbituric acid (prepared according to Example 1a) are dispersed in 250 g of water in a dissolver (Dispermat) with beads (ø 1.2 to 1.4 mm) for 6 hours at 1000 rpm. The product is isolated by filtration, washed with water and dried at 80° C. in a vacuum oven.

Comparative Example 10b

The procedure of Example 11a is repeated with the exception that the suspension is dispersed without beads for 6 hours at 1000 rpm. The product is isolated by filtration, washed with water and dried at 80° C. in a vacuum oven.

Example 11

107.6 g of Pigment Yellow 139 (crude pigment) and 46.1 g of barbituric acid are blended with 340 g of sodium chloride and 133 g of diacetone alcohol in a 1l Z-blade kneader and kneaded for 3 hours at 40° C. The resulting paste is then dispersed in 3 l of water, the product is isolated by filtration, washed salt-free with water and dried in a vacuum oven overnight at 80° C.

Comparative Example 6a

Paliotol K 1841 applied with the corresponding amount of the pigment composition.

Comparative Example 6b (Physically Mixed Blend)

85 g of Pigment Yellow 139 (crude pigment) and 50 g of a 1:1 adduct of melamine and barbituric acid (prepared according to Example 1a) are dispersed in 450 g of water with a teeth-stirrer for 30 min at 1000 rpm to form a homogenous suspension. The product is isolated by filtration, washed with water and dried at 80° C. in a vacuum oven.

The coloristic data are shown in Table 6.

Application Example A: Alkyd Melamine (AM) Paint (Full Shade)

The components are carefully blended during 20 min by 1450 rpm to prepare the alkyd resin A:
150 g of Alkydal F310 (60 wt.-% in SN100) (short oil alkyd resin; Bayer)
47.5 g of xylene (mixture of isomers)
5.0 g of butanol
5.0 g of 1-methoxy-2-propanol
2.5 g of Baysilone MA (1 wt.-% in xylene) (silicone oil; Bayer)
In order to prepare the alkyd melamine paint B
34.27 g of alkyd resin A;
4 g of a pigment composition (Examples 1 to 11);
12 g of DisperByk-161 (dispersant; high molecular weight block copolymer with pigment affinic groups; BYK); and
10.53 g of Maprenal MF650 (cross-linking agent based on a melamine resin; UCB); are dispersed in a shaker (Skandex) for 1 hour with glass beads (ø 2 mm).

The alkyd melamine paints are applied as full shade on a Leneta black/white contrast carton (wet application of a thickness of 100 μm). After a flash time of 30 min the paints are dried at 120° C. for 30 min.

Application Example B: White Reduction

A white paint containing 74 g of alkyd resin A, 0.5 g of Aerosil 200 (Evonik) and 25 g of $TiO_2$ (Kronos 2310) is used. 4.76 g of the alkyd melamine paint B made in Application Example A are blended with 15.24 g of the white paint.

The paints as white reduction are applied on a Leneta black/white contrast carton (wet application of a thickness of 100 μm), after a flash time of 30 min the paints are dried at 120° C. for 30 min.

Application Example C

The pigment prepared in Example 3b (4 wt. %) are dispersed in a conventional nitrocellulose ink composition (Skandex; 30 min).

The ink is applied as full shade on a Leneta black/white contrast carton (wet application of a thickness of 12 μm).

TABLE 1a (Pigment Red 255; full shade; Application Example A)

| Example | Content of pigment (a) (wt. %) | L* | C* | h |
|---|---|---|---|---|
| Ex. 1b | 55 | 49.4 | 67.0 | 33.3 |
| Ex. 1c | 55 | 49.3 | 67.2 | 32.9 |
| Comp. Ex. 1a | 100 | 45.4 | 61.3 | 29.2 |
| Comp. Ex. 1b | 100 | 49.4 | 67.0 | 33.3 |

TABLE 1b (Pigment Red 255; white reduction; Application Example B)

| Example | Content of pigment (a) (wt. %) | L* | C* | h |
|---|---|---|---|---|
| Ex. 1b | 55 | 70.2 | 42.5 | 23.2 |
| Ex. 1c | 55 | 70.4 | 41.7 | 22.4 |
| Ex. 1d | 55 | 68.1 | 45.1 | 24.0 |
| Comp. Ex. 1a | 100 | 69.9 | 36.3 | 18.4 |
| Comp. Ex. 1b | 100 | 69.1 | 43.3 | 22.9 |

TABLE 1c (Pigment Red 255; white reduction; Application Example B)

| Example | Content of pigment (a) (wt. %) | Color strength | Intrinsic color strength** |
|---|---|---|---|
| Comp. Ex. 1a | 100 | 100* | 100 |
| Comp. Ex. 1b | 100 | 116 | 116 |
| Ex. 1b | 55 | 122 | 223 |

*Color strength of Comp. Ex. 1a as a reference (= 100)
**Color strength re-calculated for 100 wt % pigment

TABLE 2

(Pigment Orange 73; white reduction; Application Example B)

| Example | Content of pigment (a) (wt. %) | L* | C* | h |
|---|---|---|---|---|
| Ex. 2b | 70 | 73.3 | 46.2 | 27.5 |
| Comp. Ex. 2 | 100 | 74.0 | 44.1 | 25.4 |

TABLE 3a (Pigment Violet 37; white reduction; Application Example B)

| Example | Content of pigment (a) (wt. %) | L* | C* | h |
|---|---|---|---|---|
| Ex. 3b | 70 | 44.9 | 40.2 | 299.9 |
| Comp. Ex. 3 | 100 | 44.4 | 33.7 | 295.2 |

TABLE 3b (Pigment Violet 37; full shade; Application Example C)

| Example | Content of pigment (a) (wt. %) | L* | C* | h |
|---|---|---|---|---|
| Ex. 3b | 70 | 30.3 | 50.4 | 310.6 |
| Comp. Ex. 3 | 100 | 28.6 | 38.7 | 309.8 |

TABLE 4

(Pigment Violet 19; white reduction; Application Example B)

| Example | Content of pigment (a) (wt. %) | L* | C* | h |
|---|---|---|---|---|
| Ex. 4b | 70 | 67.2 | 42.1 | 352.3 |
| Comp. Ex. 4 | 100 | 65.3 | 36.9 | 355.2 |

TABLE 5a (Pigment Blue 15.3; full shade; Application Example A)

| Example | Content of pigment (a) (wt. %) | L* | C* | h |
|---|---|---|---|---|
| Ex. 5b | 70 | 28.7 | 20.1 | 275.0 |
| Comp. Ex. 5 | 100 | 27.6 | 15.4 | 281.7 |

TABLE 5b (Pigment Blue 15.3; full shade; Application Example C)

| Example | Content of pigment (a) (wt. %) | L* | C* | h |
|---|---|---|---|---|
| Ex. 5b | 70 | 56.3 | 51.8 | 234.9 |
| Comp. Ex. 5 | 100 | 51.1 | 49.8 | 239.3 |

TABLE 6

(Pigment Yellow 139; white reduction; Application Example B)

| Pigment composition | Content of pigment (a) (wt. %) | Color strength | Intrinsic color strength** |
|---|---|---|---|
| Comp. Ex. 6a | 100 | 100* | 100 |
| Comp. Ex. 6b | 55 | 55 | 100 |
| Ex. 6b | 55 | 119 | 216 |
| Ex. 11 | 70 | 108 | 154 |

*Color strength of Comp. Ex. 1a as a reference (= 100)
**Color strength re-calculated for 100 wt. % pigment

The invention claimed is:

1. A pigment composition, comprising:
(a) an organic pigment, and
(b) an adduct selected from
(b1) an adduct containing a compound of formula $$\text{(I)}$$

or a tautomeric form thereof, wherein

X is O, S or $NR^1$;

Y is O, S or $NR^1$;

-A-B— is selected from the group consisting of $-CR^2=CR^3-$, $-CR^4R^5-CR^6R^7-$, $-CY-CR^8R^9-$, $-CX-NR^{10}-$, $CR^{11}=N-$, $-CR^{12}R^{13}-NR^{14}-$ and $$\text{structure}$$

$R^1$ is hydrogen, $C_1$-$C_8$alkyl, $C_3$-$C_7$cycloalkyl, $C_6$-$C_{10}$aryl or $C_7$-$C_{10}$aralkyl;

$R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, halogen, $C_1$-$C_8$alkyl, $C_2$-$C_8$alkenyl or $C_6$-$C_{10}$aryl, or $R^2$ and $R^3$ form a benzoannellated ring;

said alkyl, cycloalkyl or alkenyl is unsubstituted or substituted with halogen or OH;

said aryl or benzoannellated ring is unsubstituted or substituted with halogen, OH or $C_1$-$C_4$alkyl;

and a compound of formula $$\text{(II)}$$

or a tautomeric form thereof, wherein

Z is N or $CR^{18}$;

$R^{18}$ is hydrogen, $C_1$-$C_8$alkyl, $C_2$-$C_8$alkenyl, $C_6$-$C_{10}$aryl or $C_7$-$C_{10}$aralkyl;

$R^{15}$, $R^{16}$ and $R^{17}$ are independently of each other hydrogen, $C_1$-$C_8$alkyl, $C_6$-$C_{10}$aryl, $C_7$-$C_{10}$aralkyl or a group of formula

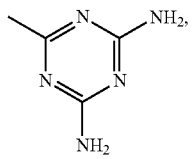

(III)

said alkyl or alkenyl is unsubstituted or substituted with halogen or OH,
said aryl is unsubstituted or substituted with halogen, OH or $C_1$-$C_4$alkyl; or
(b2) an adduct containing a compound of formula

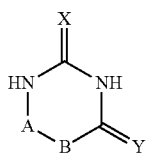

(I)

or a tautomeric form thereof, wherein
X is O, S or $NR^1$;
Y is O, S or $NR^1$;
—A-B— is selected from the group consisting of —$CR^2$=$CR^3$—, —$CR^4R^5$—$CR^6R^7$—, —CY—$CR^8R^9$—, —CX—$NR^{10}$—, —$CR^{11}$=N—, —$CR^{12}R^{13}$—$NR^{14}$— and

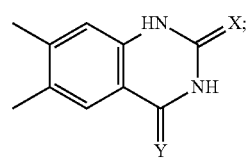

$R^1$ is hydrogen, $C_1$-$C_8$alkyl, $C_3$-$C_7$cycloalkyl, $C_6$-$C_{10}$aryl or $C_7$-$C_{10}$aralkyl;
$R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, halogen, $C_1$-$C_8$alkyl, $C_2$-$C_8$alkenyl or $C_6$-$C_{10}$aryl, or
$R^2$ and $R^3$ form a benzoannellated ring;
said alkyl, cycloalkyl or alkenyl is unsubstituted or substituted with halogen or OH;
said aryl or benzoannellated ring is unsubstituted or substituted with halogen, OH or $C_1$-$C_4$alkyl; or
(b3) an adduct containing a compound of formula

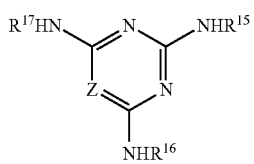

(II)

or a tautomeric form thereof, wherein
Z is N or $CR^{18}$;
$R^{18}$ is hydrogen, $C_1$-$C_8$alkyl, $C_2$-$C_8$alkenyl, $C_6$-$C_{10}$aryl or $C_7$-$C_{10}$aralkyl;

$R^{15}$, $R^{16}$ and $R^{17}$ are independently of each other hydrogen, $C_1$-$C_8$alkyl, $C_6$-$C_{10}$aryl, $C_7$-$C_{10}$aralkyl or a group of formula

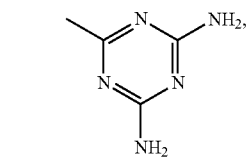

(III)

said alkyl or alkenyl is unsubstituted or substituted with halogen or OH, and
said aryl is unsubstituted or substituted with halogen, OH or $C_1$-$C_4$alkyl;
wherein the organic pigment is selected from a diketopyrrolopyrrole, isoindoline, isoindolinone, phthalocyanine, quinacridone, quinophthalone, dioxazine pigment or a mixture of said pigments.

2. The pigment composition according to claim 1, comprising adduct (b1), wherein
the adduct (b1) contains the compound of formula (I) or a tautomeric form thereof,
wherein X and Y are O; -A-B— is —CY—$CR^8R^9$— or —CX—$NR^{10}$—;
$R^8$, $R^9$ and $R^{10}$ are hydrogen; and
the compound of formula (II) or a tautomeric form thereof, wherein
Z is N; and $R^{15}$, $R^{16}$ and $R^{17}$ are independently of each other hydrogen or $C_1$-$C_4$alkyl.

3. The pigment composition according to claim 1, comprising adduct (b1), wherein the adduct (b1) contains the compound of formula (I) or a tautomeric form thereof,
wherein X and Y are O; -A-B— is —CY—$CR^8R^9$— or —CX—$NR^{10}$—;
$R^8$, $R^9$ and $R^{10}$ are hydrogen; and
the compound of formula (II) or a tautomeric form thereof, wherein
Z is $CR^{18}$; $R^{18}$ is hydrogen, $C_1$-$C_4$alkyl, phenyl or $C_7$-$C_{10}$aralkyl; and
$R^{15}$, $R^{16}$ and $R^{17}$ are independently of each other hydrogen or $C_1$-$C_4$alkyl.

4. The pigment composition according to claim 1, comprising adduct (bp, wherein the adduct (b1) contains the compound of formula (I) or a tautomeric form thereof,
wherein X and Y are O; -A-B— is —CY—$CR^8R^9$— or —CX—$NR^{10}$—;
$R^8$, $R^9$ and $R^{10}$ are hydrogen; and
the compound of formula (II) or a tautomeric form thereof,
wherein Z is N; and $R^{15}$, $R^{16}$ and $R^{17}$ are hydrogen.

5. The pigment composition according to claim 1, comprising adduct (b3), wherein the adduct (b3) contains the compound of formula (II) or a tautomeric form thereof, and a compound of formula HOOC—$R^{19}$—COOH (IV), wherein
$R^{19}$ is a direct bond, $C_1$-$C_8$alkylene, $C_2$-$C_8$alkenylene, $C_3$-$C_7$cycloalkylene or
$C_6$-$C_{10}$arylene;
said alkylene, cycloalkylene or alkenylene is unsubstituted or substituted with halogen or OH, and said alkylene may further be interrupted by O, S, $NR^{20}$, phenyl, naphthyl or cyclohexylene,
said arylene is unsubstituted or substituted with halogen, OH or $C_1$-$C_4$alkyl; and
$R^{20}$ is hydrogen or $C_1$-$C_4$alkyl.

6. The pigment composition according to claim 1, wherein the mole ratio of the compound of formula (I) to the compound of formula (II) is from 0.4:0.6 to 0.7:0.3.

7. The pigment composition according to claim 1, comprising adduct (b2), wherein the adduct (b2) is formed of a compound of formula (I) or a tautomeric form thereof, wherein
X and Y are O;
-A-B— is selected from the group consisting of —CR²=CR³—, —CY—CR⁸R⁹— and —CX—NR¹⁰—;
R², R³ and R¹⁰ are hydrogen; and
R⁸ and R⁹ are independently of each other hydrogen, halogen or $C_1$-$C_4$alkyl.

8. The pigment composition according to claim 1, wherein the weight ratio of component (a) to component (b) is of from 0.85:0.15 to 0.5:0.5.

9. The pigment composition according to claim 1, wherein the pigment composition consists essentially of component (a) and component (b).

10. The pigment composition according to claim 1, wherein the weight ratio of component (a) to component (b) is from 0.80:0.2 to 0.65:0.35.

11. The pigment composition according to claim 1, comprising adduct (b1).

12. The pigment composition according to claim 1, comprising adduct (b2).

13. The pigment composition according to claim 1, comprising adduct (b3).

14. A process for preparing a pigment composition, as defined in claim 1, which process comprises treating (a) an organic pigment with an adduct (b) selected from an adduct (b1), (b2) or (b3).

15. The process according to claim 14, wherein the organic pigment is treated with the adduct (b) using salt kneading, wet milling or dispersing,
wherein optionally the adduct is prepared in situ during the treating step.

16. The process according to claim 14, wherein the organic pigment is treated with the adduct (b) using salt kneading or wet milling,
wherein optionally the adduct is prepared in situ during the treating step.

17. A pigment composition, obtained by a process according to claim 14.

18. A coating composition, a paint, a printing ink, a liquid ink, plastics, a film or a fiber, which is colored with a pigment composition, as defined in claim 1.

19. A process for coloring a coating composition, a paint, a printing ink, a liquid ink, plastics, a film or a fiber, which process comprises adding thereto a pigment composition, as defined in claim 1.

20. A process of stabilizing a dioxazine pigment, the process comprising
adding, to a dioxazine pigment, an adduct (b) selected from
(b1) an adduct containing a compound of formula

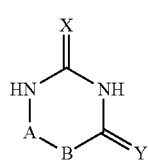

(I)

or a tautomeric form thereof, wherein

X is O, S or NR¹;

Y is O, S or NR¹;

-A-B— is selected from the group consisting of —CR²=CR³—, —CR⁴R⁵—CR⁶R⁷—, —CY—CR⁸R⁹—, —CX—NR¹⁰—, —CR¹¹=N—, —CR¹²R¹³—NR¹⁴— and

R¹ is hydrogen, $C_1$-$C_8$alkyl, $C_3$-$C_7$cycloalkyl, $C_6$-$C_{10}$aryl or $C_7$-$C_{10}$aralkyl; R², R³, R⁴, R⁵R⁶, R⁷, R⁸, R⁹, R¹⁰, R¹¹, R¹², R¹³ and R¹⁴ are independently of each other hydrogen, halogen, $C_1$-$C_8$alkyl, $C_2$-$C_8$alkenyl or $C_6$-$C_{10}$aryl, or R² and R³ form a benzoannellated ring;

said alkyl, cycloalkyl or alkenyl is unsubstituted or substituted with halogen or OH;

said aryl or benzoannellated ring is unsubstituted or substituted with halogen, OH or $C_1$-$C_4$alkyl;

and a compound of formula

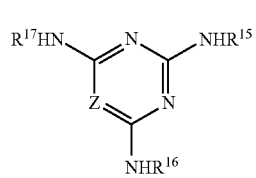

(II)

or a tautomeric form thereof, wherein

Z is N or CR¹⁸;

R¹⁸ is hydrogen, $C_1$-$C_8$alkyl, $C_2$-$C_8$alkenyl, $C_6$-$C_{10}$aryl or $C_7$-$C_{10}$aralkyl;

R¹⁵, R¹⁶ and R¹⁷ are independently of each other hydrogen, $C_1$-$C_8$alkyl, $C_6$-$C_{10}$aryl, $C_7$-$C_{10}$aralkyl or a group of formula

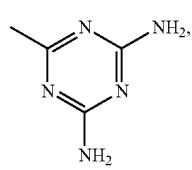

(III)

said alkyl or alkenyl is unsubstituted or substituted with halogen or OH, said aryl is unsubstituted or substituted with halogen, OH or $C_1$-$C_4$alkyl;
or
(b2) an adduct containing a compound of formula

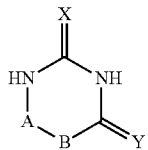
(I)

or a tautomeric form thereof, wherein
X is O, S or $NR^1$;
Y is O, S or $NR^1$;
-A-B— is selected from the group consisting of —$CR^2$=$CR^3$—, —$CR^4R^5$—$CR^6R^7$—, —CY—$CR^8R^9$—, —CX—$NR^{10}$, —$CR^{11}$=N—, —$CR^{12}R^{13}$—$NR^{14}$— and

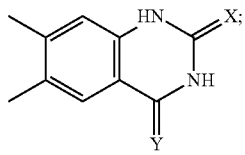

$R^1$ is hydrogen, $C_1$-$C_8$alkyl, $C_3$-$C_7$cycloalkyl, $C_6$-$C_{10}$aryl or $C_7$-$C_{10}$aralkyl;
$R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, halogen, $C_1$-$C_8$alkyl, $C_2$-$C_8$alkenyl or $C_6$-$C_{10}$aryl, or $R^2$ and $R^3$ form a benzoannellated ring;
said alkyl, cycloalkyl or alkenyl is unsubstituted or substituted with halogen or OH;

said aryl or benzoannellated ring is unsubstituted or substituted with halogen, OH or $C_1$-$C_4$alkyl;
or
(b3) an adduct containing a compound of formula

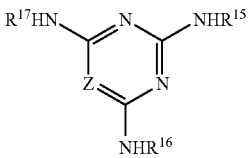
(II)

or a tautomeric form thereof, wherein
Z is N or $CR^{18}$;
$R^{18}$ is hydrogen, $C_1$-$C_8$alkyl, $C_2$-$C_8$alkenyl, $C_6$-$C_{10}$aryl or $C_7$-$C_{10}$aralkyl;
$R^{15}$, $R^{16}$ and $R^{17}$ are independently of each other hydrogen, $C_1$-$C_8$alkyl, $C_6$-$C_{10}$aryl, $C_7$-$C_{10}$aralkyl or a group of formula

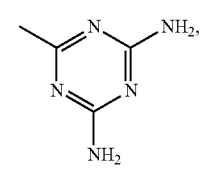
(III)

said alkyl or alkenyl is unsubstituted or substituted with halogen or OH, and
said aryl is unsubstituted or substituted with halogen, OH or $C_1$-$C_4$alkyl.

* * * * *